(12) United States Patent
Wei et al.

(10) Patent No.: US 8,334,104 B2
(45) Date of Patent: Dec. 18, 2012

(54) METHODS FOR DETECTION OF HYDROPHOBIC DRUGS

(75) Inventors: Tie Q. Wei, Bear, DE (US); Alan Craig, Wilmington, DE (US); Amy Posey, Cochranville, PA (US)

(73) Assignee: Siemens Healthcare Diagnostics Inc., Tarrytow, NY (US)

( * ) Notice: Subject to any disclaimer, the term of this patent is extended or adjusted under 35 U.S.C. 154(b) by 0 days.

(21) Appl. No.: 13/282,957

(22) Filed: Oct. 27, 2011

(65) Prior Publication Data

US 2012/0064546 A1    Mar. 15, 2012

Related U.S. Application Data

(62) Division of application No. 13/026,756, filed on Feb. 14, 2011, now Pat. No. 8,071,317, which is a division of application No. 11/956,603, filed on Dec. 14, 2007, now Pat. No. 7,910,378.

(51) Int. Cl.
*G01N 33/557* (2006.01)
*G01N 33/543* (2006.01)
*G01N 1/18* (2006.01)

(52) U.S. Cl. .......... 435/7.1; 435/7.8; 435/962; 436/507; 436/517; 436/518; 436/523; 436/528; 436/538; 436/545; 436/546; 436/172; 436/175; 436/177; 436/815; 424/9.2

(58) Field of Classification Search ............ 435/7.1, 435/7.21, 7.8, 7.9, 7.93, 7.94, 962; 436/507, 436/517, 522, 526, 536, 538, 545, 546, 17, 436/18, 175, 176, 177, 178, 179, 815, 518, 436/523, 528, 56, 164, 166, 172; 424/9.2; 530/321, 350, 363, 402

See application file for complete search history.

(56) References Cited

U.S. PATENT DOCUMENTS

| | | | |
|---|---|---|---|
| 5,135,875 A | 8/1992 | Meucci et al. | |
| 5,340,716 A | 8/1994 | Ullman et al. | |
| 5,565,326 A | 10/1996 | Daiss et al. | |
| 5,650,288 A | 7/1997 | MacFarlane et al. | |
| 6,171,801 B1 | 1/2001 | Staples et al. | |
| 6,187,547 B1 | 2/2001 | Legay et al. | |
| 6,190,873 B1 | 2/2001 | Davalian et al. | |
| 6,225,073 B1 | 5/2001 | Alexander et al. | |
| 6,777,190 B1 | 8/2004 | Buechler et al. | |
| 6,790,668 B1 | 9/2004 | Ferreira et al. | |
| 6,825,000 B1 | 11/2004 | Yokoi et al. | |
| 6,887,669 B1 | 5/2005 | Staples et al. | |
| 7,186,518 B2 | 3/2007 | Wang et al. | |
| 2005/0112778 A1* | 5/2005 | Wang et al. | 436/501 |
| 2006/0246518 A1 | 11/2006 | Chen et al. | |
| 2007/0087396 A1 | 4/2007 | Konrath et al. | |
| 2007/0122913 A1 | 5/2007 | Tanaka et al. | |
| 2008/0311676 A1* | 12/2008 | Brate et al. | 436/501 |

FOREIGN PATENT DOCUMENTS

| | | |
|---|---|---|
| EP | 0 471 295 A1 | 2/1992 |
| WO | 2008/082974 A2 | 7/2008 |
| WO | 2008/147982 A1 | 12/2008 |

OTHER PUBLICATIONS

Simamora P et al: "Solubilization of Rapamycin", International Journal of Pharmaceutics, Elsevier BV, NL, vol. 213, No. 1-2, Feb. 1, 2001, pp. 25-29, XP002571642, ISSN: 0378-5173, DOI: DOI: 10.1016/S0378-5173(00)00617-7.

* cited by examiner

*Primary Examiner* — Gail R Gabel
(74) *Attorney, Agent, or Firm* — Theodore J. Leitereg

(57) ABSTRACT

Methods and reagents are disclosed for pretreating a sample suspected of containing a hydrophobic drug for conducting an assay method for detecting the hydrophobic drug. A combination is provided in a medium that includes the sample, a releasing agent for releasing the hydrophobic drug and the metabolites from endogenous binding moieties, and a selective solubility agent that provides for substantially equal solubility of the hydrophobic drug and the metabolites in the medium. The selective solubility agent includes a water miscible, non-volatile organic solvent and is present in the medium in a concentration sufficient to provide for substantially equal solubility of the hydrophobic drug and the metabolites in the medium. The medium, which may further include a hemolytic agent, is incubated under conditions for releasing the hydrophobic drug and the metabolites from endogenous binding moieties. The pretreated sample may be subjected to an assay for determining the hydrophobic drug.

6 Claims, No Drawings

METHODS FOR DETECTION OF HYDROPHOBIC DRUGS

CROSS-REFERENCE TO RELATED APPLICATION

This application is a Divisional of U.S. patent application Ser. No. 13/026,756 filed on Feb. 14, 2011, now U.S. Pat. No. 8,071,317, which is a Divisional of U.S. patent application Ser. No. 11/956,603 filed on Dec. 14, 2007, now U.S. Pat. No. 7,910,378.

BACKGROUND

The invention relates to compounds, methods and kits for the determination of hydrophobic drugs such as, for example, immunosuppressant drugs, in samples, such as patient samples, known or suspected to contain one or more of such hydrophobic drugs.

The body relies upon a complex immune response system to distinguish self from non-self. At times, the body's immune system must be controlled in order to either augment a deficient response or suppress an excessive response. For example, when organs such as kidney, heart, heart-lung, bone marrow and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK or tacrolimus). Another drug that finds use as an immunosuppressant in the United States and other countries is sirolimus, also known as rapamycin. Derivatives of sirolimus are also said to be useful as immunosuppressants. Such derivatives include, for example, Everolimus, and the like.

The side effects associated with some immunosuppressant drugs can be controlled in part by carefully controlling the level of the drug present in a patient. Therapeutic monitoring of concentrations of immunosuppressant drugs and related drugs in blood is required to optimize dosing regimes to ensure maximal immunosuppression with minimal toxicity. Although immunosuppressant drugs are highly effective immunosuppressive agents, their use must be carefully managed because the effective dose range is often narrow and excessive dosage can result in serious side effects. On the other hand, too little dosage of an immunosuppressant can lead to tissue rejection. Because the distribution and metabolism of an immunosuppressant drug can vary greatly between patients and because of the wide range and severity of adverse reactions, accurate monitoring of the drug level is essential.

In therapeutic drug monitoring field, selectively detecting the parent drug over its metabolites is often an important goal for designing immunoassays. This is especially true for immunosuppressant drugs. For that reason, HPLC tandem MS assays have become standard methods for the measurement of sirolimus and other immunosuppressant drugs due to their ability to selectively measure the parent drug.

Most whole blood assays for immunosuppressant drugs require a manual step using reagents to extract the drug from blood constituents. As a result, the drug molecules and drug metabolite molecules are dissociated from endogenous binding proteins and are extracted into a relatively clean solution in which plasma proteins and lipoprotein particles as well as most other molecules are removed. Because precipitation techniques are usually used, the extracted sample is basically free of most blood macromolecules including drug-binding proteins. Thus, in the extracted samples, the parent drug and its metabolites are dissolved as unbound, individual molecules and compete with one another for reaction with an assay antibody in the immunoreaction mixture. The binding of assay antibody to the drug occurs in the absence of most endogenous substances in these assays. The cross-reactivity of a drug metabolite depends mostly on its antibody binding affinity in such assays.

In a homogeneous assay for an immunosuppressant drug where there is no manual extraction or separation of the drug from blood constituents, an antibody for the immunosuppressant drug has to detect the drug in the presence of most or all blood constituents, the presence of which might interfere with the binding of the antibody to the immunosuppressant drug. Furthermore, the samples contain metabolites of the drug and high metabolite cross-reactivity presents a serious accuracy issue in assays for immunosuppressant drugs.

There is, therefore, a continuing need to develop fast and accurate diagnostic methods to measure levels of immunosuppressant drugs or derivatives thereof in patients. The methods should be fully automated and be accurate even when conducted on whole blood samples with no-extraction using a homogeneous assay where an antibody employed in the assay has to detect the drug in the presence of most, if not all, blood constituents and in the presence of drug metabolites. The assay should selectively detect the parent drug while minimizing inaccuracies resulting from the cross-reactivity of its metabolites.

SUMMARY

One embodiment of the present invention is a method for selectively enhancing the bioavailability of a hydrophobic drug over metabolites of the hydrophobic drug. A combination is provided in a medium. The combination comprises (i) the sample, (ii) a releasing agent for releasing the hydrophobic drug and its metabolites from endogenous binding moieties, and (iii) a selective solubility agent that provides for enhancement of the bioavailability of the hydrophobic drug over that of the metabolites in the medium. The selective solubility agent comprises a water miscible, non-volatile organic solvent and is present in the medium in a concentration sufficient to enhance the bioavailability of the hydrophobic drug over that of the metabolites in the medium. The medium is incubated under conditions for enhancing the bioavailability of the hydrophobic drug over that of the metabolites.

Another embodiment of the present invention is a method for determining a hydrophobic drug in a sample suspected of containing a hydrophobic drug. A combination is provided in a medium. The combination comprises the sample, a releasing agent for releasing the hydrophobic drug and its metabolites from endogenous binding moieties, and a selective solubility agent that provides for enhancement of the bioavailability of the hydrophobic drug over that of the metabolites in the medium, wherein the selective solubility agent comprises a water miscible, non-volatile organic solvent and wherein the concentration of the selective solubility agent in the medium is sufficient to enhance the bioavailability of the hydrophobic drug over that of the metabolites in the medium. The combination in the medium further comprises a hemolytic agent. The medium is incubated under conditions for hemolyzing cells in the sample and for enhancing the bioavailability of the hydrophobic drug over that of the metabolites. To the medium is added reagents for determining the presence and/or amount of the hydrophobic drug in the sample wherein the reagents comprise at least one antibody for the hydrophobic drug. The medium is examined for the presence of a complex comprising the hydrophobic drug and the antibody for the hydrophobic drug, the presence and/or amount of the complex indicating the presence and/or amount of the hydrophobic drug in the sample.

Another embodiment of the present invention is a method for determining an immunosuppressant drug in a sample suspected of containing an immunosuppressant drug. A combination is formed in a medium wherein the combination comprises the sample, a releasing agent for releasing the immunosuppressant drug and its metabolites from endogenous binding moieties and a selective solubility agent that provides for enhancement of the bioavailability of the hydrophobic drug over that of the metabolites in the medium. The selective solubility agent comprises a water miscible, non-volatile organic solvent. The concentration of the selective solubility agent in the medium is sufficient to provide for enhancement of the bioavailability of the hydrophobic drug over that of the metabolites in the medium. The medium is incubated under conditions for releasing the immunosuppressant drug and its metabolites from endogenous binding moieties. To the medium is added (i) a reagent comprising (I) an antibody for the immunosuppressant drug and (II) an enzyme and (ii) magnetic particles comprising the immunosuppressant drug or an analog thereof. The medium is examined for the presence of a complex comprising the immunosuppressant drug and the antibody for the immunosuppressant drug, the presence and/or amount of the complex indicating the presence and/or amount of the immunosuppressant drug in the sample.

Another embodiment of the present invention is a method for determining an immunosuppressant drug in a sample suspected of containing an immunosuppressant drug. A combination is formed in a medium wherein the combination comprises the sample, a releasing agent for releasing the immunosuppressant drug and its metabolites from endogenous binding moieties and a selective solubility agent that provides for enhancement of the bioavailability of the hydrophobic drug over that of the metabolites in the medium. The selective solubility agent comprises a water miscible, non-volatile organic solvent and the concentration of the selective solubility agent in the medium is sufficient to provide for enhancement of the bioavailability of the hydrophobic drug over that of the metabolites in the medium. The medium is incubated under conditions for enhancing the bioavailability of the hydrophobic drug over that of the metabolites. To the medium is added (i) a photosensitizer associated with a first particle and being capable of generating singlet oxygen, and (ii) a chemiluminescent composition activatable by singlet oxygen and associated with a second particle, wherein an antibody for the immunosuppressant drug is associated with the first particle or the second particle or both. The combination is subjected to conditions for binding of the antibody to the immunosuppressant drug, if present. The photosensitizer is irradiated with light and the amount of luminescence generated by the chemiluminescent composition is detected. The amount of luminescence is related to the amount of the immunosuppressant drug in the sample.

Alternatively, in the above embodiment, one of the first particle or the second particle comprises the antibody and the other particle comprises a drug analog for the immunosuppressant drug. The combination is subjected to conditions for competition of the drug analog coated particles and the immunosuppressant drug, if present, to the antibody for the drug. Alternatively, in the above embodiment, the first particle or the second particle comprises streptavidin, which combines with a biotinylated analog for the immunosuppressant drug in the medium. The combination is subjected to conditions for competition of biotinylated drug analog and the immunosuppressant drug for the antibody for the drug. In either of the above alternative embodiments, the photosensitizer is irradiated with light and the amount of luminescence generated by the chemiluminescent composition is detected. The amount of luminescence is related to the amount of the immunosuppressant drug in the sample.

DETAILED DESCRIPTION OF SPECIFIC EMBODIMENTS

General Discussion

The present inventors have recognized that the cross-reactivity of drug metabolites can be reduced by making the drug and metabolites less protein-bound and enhancing the solubility of the hydrophobic drug in an assay mixture relative to metabolites of the hydrophobic drug, which the present inventors recognized as more hydrophilic than the drug itself. The more hydrophilic nature of the drug metabolites appears to be due to extra hydroxyl groups that result from drug metabolism through the liver by demethylation and hydroxylation. Hydrophobic interaction is an important and common mechanism for drug-protein binding in aqueous blood. The present inventors observed that hydrophilic metabolites tend to have lower affinity to the binding proteins and diffuse more freely in aqueous blood and assay mixture. For that reason a larger portion of the metabolite molecules are free, non-protein bound and more accessible to the assay antibody than the parent drug in the aqueous assay mixture. Assuming that a drug metabolite has the same binding affinity to the assay antibody as the parent drug, the metabolite will form more immuno-complexes with the antibody than the parent drug due to its higher accessibility. The above recognition is contrary to a common belief that metabolite cross-reactivity is only a function of antibody binding affinity. The present inventors have determined that the cross-reactivity of a metabolite in such assays depends not only on its antibody binding affinity but also on its binding affinity to the endogenous binding proteins.

Embodiments of the assays described herein are homogeneous immunoassays, which may also be referred to as essentially partition-free immunoassays. Embodiments of the present assays selectively detect the parent drug while minimizing the cross-reactivity of an antibody for the drug to the metabolites of such drug. The use of selective solubility agents that are water miscible, non-volatile organic solvents in a sample partition-free assay selectively increases the bioavailability of the parent drug over that of the metabolites, and selectively increases the accessibility of the hydrophobic drug to the assay antibody over the metabolites. The solubility differentials rearranged by the above selective solubility agents over regular aqueous reagent solutions minimizes the detection of more hydrophilic metabolites and enhances the detection of the parent hydrophobic drug. That is, the selective solubility agents of the invention selectively increase the bioavailability of the parent drug over the metabolites. Thus, the selective solubility agents added to an assay medium adjust the selectivity or bioavailability of the hydrophobic drug relative to aqueous media that are customarily employed in such assays. The selective solubility agents may also enhance the bioavailability of a hydrophobic antibody that is employed in an assay.

The current methods focus on the mitigation of inaccurate assay results caused by cross-reactivity of drug metabolites with the antibody reagent employed in an immunoassay. The present methods have application to fully automated homogeneous assays in which, prior to the assay, there is no extraction or separation of the hydrophobic drug from other constituents of the sample including drug metabolites. In a "non-manual extraction" assay, a sample such as a whole blood sample is combined with a hemolyzing agent and a releasing agent in a medium and, following an incubation period to allow for hemolysis and release of the drug from other blood constituents, reagents for conducting an assay for the hydrophobic drug are added to the medium and the assay is conducted. It has been found that the bioavailability of a hydrophobic drug in an assay for the drug may be enhanced relative to the metabolites of the drug by incubating a sample suspected of containing the hydrophobic drug with a releasing agent and a selective solubility agent that enhances the availability of the hydrophobic drug for subsequent binding to an antibody for the drug during an assay to detect the presence and/or amount of the drug wherein other constituents of the sample are present.

The term "hydrophobic drug" as used herein refers to a drug, usually a therapeutic drug, where the drug exhibits a characteristic of absorption by a lipophilic moiety such as, for example, a lipoprotein, or of reduced solubility in a polar medium. The absorption or lack of solubility is such that it interferes with the quantitation of the drug in an assay for the drug. Interference with the quantitation of the drug means that the ability to make an accurate quantitative determination of the drug in an assay is reduced by at least about 10%, by at least about 15%, by at least about 20%, by at least about 25%, by at least about 30%, and so forth. A "hydrophobic antibody" is an antibody that exhibits reduced solubility in an aqueous medium as compared to other antibodies.

Immunosuppressant drugs are an example of hydrophobic drugs. Immunosuppressant drugs are therapeutic drugs that are administered to transplant recipients in order to help prevent allograft rejection of non-self tissue. Immunosuppressive drugs can be classified as follows: glucocorticoids, cytostatics, antibodies, drugs acting on immunophilins, and other drugs such as interferons, opiates INF binding proteins, mycophenolate, FTY720 and the like. A particular class of immunosuppressant drugs comprises those drugs that act on immunophilins. Immunophilins are an example of high-affinity, specific binding proteins having physiological significance Two distinct families of immunophilins are presently known: cyclophilins and macrophilins, the latter of which specifically bind, for example, tacrolimus or sirolimus. The immunosuppressant drugs that act on immunophilin include, for example, cyclosporin (including cyclosporin A, cyclosporin B, cyclosporin C, cyclosporin D, cyclosporin E, cyclosporin F, cyclosporin G, cyclosporin H, cyclosporin I), tacrolimus (FK506, PROGRAF®), sirolimus (rapamycin, RAPAMUNE®), everolimus (RAD, CERTICAN®) and so forth.

The term "bioavailability" as used herein with respect to a "hydrophobic drug" refers to the amount of hydrophobic drug in a sample that is available for measurement such as, for example, available for binding to an antibody for the hydrophobic drug particularly in an assay where there are constituents in the sample to be analyzed such as metabolites of the drug that cross-react with an antibody for the drug, thereby interfering with the accuracy of an assay for the drug. A primary factor affecting bioavailability and of concern in the present methods is the presence in a sample of drug metabolites that bind to antibody for the drug and render an assay for the drug inaccurate, particularly where there is minimal or no separation of such metabolites from the drug and minimal or no separation of other components in a sample. The term "bioavailability" as used herein with respect to a "hydrophobic antibody" refers to the amount of hydrophobic antibody that is employed in an assay and that is available for binding to an analyte.

In accordance with the present embodiments, "enhanced bioavailability" or "enhancement of bioavailability" or "enhance the bioavailability" with respect to a hydrophobic drug means that there is an enhancement or increase in the amount of the hydrophobic drug available for detection in a sample that contains metabolites of the drug that cross-react with an antibody for the drug. In accordance with the present embodiments, "enhanced bioavailability" or "enhancement of bioavailability" or "enhance the bioavailability" with respect to a hydrophobic antibody means that there is an enhancement or increase in the amount of the hydrophobic antibody available for binding to an analyte.

In accordance with the present embodiments, "selectively enhanced bioavailability" or "selective enhancement of bioavailability" or "selectively enhance the bioavailability" with respect to a hydrophobic drug means that there is an enhancement or increase in the amount of the hydrophobic drug available for binding to an antibody for the hydrophobic drug and, therefore, for detection in a sample, relative to the amount of metabolites of the hydrophobic drug that cross-react with an antibody for the drug and that are available for cross-reacting with the antibody for the hydrophobic drug.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

Accordingly, as mentioned above, an embodiment of the present invention is a method for selectively enhancing the bioavailability of a hydrophobic drug over metabolites of the hydrophobic drug. A combination is formed in a medium where the combination comprises the sample, a releasing agent, and a selective solubility agent for the hydrophobic drug. The releasing agent displaces the hydrophobic drug, and its metabolites, from endogenous binding moieties. The selective solubility agent promotes equalization of the bioavailability of the hydrophobic drug and that of the metabolites in the medium. The selective solubility agent comprises a water miscible, non-volatile organic solvent and is present in the medium in a concentration sufficient to selectively enhance the bioavailability of the hydrophobic drug over that of the metabolites in the medium.

The sample to be analyzed is one that is suspected of containing one or more hydrophobic drug analytes. The sample typically comprises one or more endogenous binding moieties that bind to the hydrophobic drug. The endogenous binding moieties may be binding proteins that bind a hydrophobic drug such as a lipoprotein, e.g., a protein that comprises a lipid moiety or other substances that bind the hydrophobic drug such as cholesterol, triglyceride, and so forth. The samples are preferably from humans or animals and include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum and, in a particular embodiment the sample is whole blood. The sample is not pretreated to remove such endogenous binding moieties.

The sample can be prepared in any convenient medium that does not interfere with an assay; an aqueous medium generally is employed. The nature of the medium is discussed in more detail below. A releasing agent and a selective solubility agent for the hydrophobic drug in accordance with the present methods are combined in the medium, which may also include a hemolytic agent.

Hemolytic Agent

A hemolytic agent is a compound or mixture of compounds that disrupt the integrity of the membranes of red blood cells thereby releasing intracellular contents of the cells. Numerous hemolytic agents are known in the art. Hemolytic agents include, for example, non-ionic detergents, anionic detergents, amphoteric detergents, low ionic strength aqueous solutions (hypotonic solutions), bacterial agents, antibodies that cause complement dependent lysis, and the like. Non-ionic detergents that may be employed as the hemolytic agent include both synthetic detergents and natural detergents. Examples of synthetic detergents include TRITON™ X-100, TRITON™ N-101, TRITON™ X-114, TRITON™ X-405, TRITON™ SP-135, TWEEN® 20 (polyoxyethylene (20) sorbitan monolaurate), TWEEN® 80 (polyoxyethylene (20) sorbitan monooleate), DOWFAX®, ZONYL®, pentaerythrityl palmitate, ADOGEN® 464, ALKANOL® 6112 surfactant, allyl alcohol 1,2-butoxylate-block-ethoxylate HLB 6, BRIJ®, ethylenediamine tetrakis(ethoxylate-block-propoxylate) tetrol, IGEPAL®, MERPOL®, poly(ethylene glycol), 2-[ethyl[(heptadecafluorooctyl)sulfonyl]amino]ethyl ether, polyethylene-block-poly(ethylene glycol), polyoxyethylene sorbitan tetraoleate, polyoxyethylene sorbitol hexaoleate, TERGITOL® NP-9, GAFAC® (RHODAFAC®, an alkyl polyoxyethylene glycol phosphate ester such as, for example, alpha-dodecyl-omega-hydroxypoly(oxy-1,2-ethanediyl) phosphate), and EP110® and the like. Naturally-occurring detergents that may be employed as the hemolytic agent include, for example, saponins, sodium or potassium neutralized fatty acid, neutralized phospholipids, diacylglycerol, neutralized phosphatidyl serine, phosphatidate, neutralized phosphatidyl ethanoliamin, phosphatidyl choline, phosphatidyl inositol, phosphatidylcholine, bile salt, unesterified cholesterol, neutralized sphingosine, ceramide, and the like. Combinations of one or more synthetic detergents or one or more naturally occurring detergents and combinations of synthetic detergents and naturally occurring detergents may also be employed.

The nature and amount or concentration of hemolytic agent employed depends on the nature of the sample, the nature of the hydrophobic drug, the nature of the rest of the reagent components, the reaction conditions, and the like. The amount of the hemolytic agent is at least sufficient to cause lysis of red blood cells to release contents of the cells. In some embodiments the amount of the hemolytic agent is about 0.0001% to about 0.5%, about 0.001% to about 0.4%, about 0.01% to about 0.3%, about 0.01% to about 0.2%, about 0.1% to about 0.3%, about 0.2% to about 0.5%, about 0.1% to about 0.2%, and so forth (percent is weight/volume).

Releasing Agent

The releasing agent displaces the hydrophobic drug from endogenous binding moieties. The releasing agent can, and does in many instances, displace metabolites of the hydrophobic drug from endogenous binding moieties. In many embodiments the releasing agent has high binding affinity to the endogenous binding proteins so that it readily displaces the hydrophobic drug, and its metabolites, from endogenous binding proteins. In addition, the releasing agent does not bind to any significant degree to an antibody for the drug that is used in the assay. By the phrase "does not bind to any significant degree" is meant that the extent of binding should be low enough so that an accurate assay for the drug may be carried out. The releasing agent may be any moiety, either a single compound or a mixture of compounds, which accomplishes the desired result of displacement with no significant binding to an assay antibody. In many embodiments the releasing agent displaces the hydrophobic drug and its metabolite from endogenous binding substances to render both the hydrophobic drug and the metabolites substantially equally accessible to an antibody for the hydrophobic drug. "Substantially equally accessible" means that the amount of hydrophobic drug available for binding to antibody does not vary to any significant extent from the total amount of metabolites of the hydrophobic drug that are available for binding to the antibody. The amount of metabolites available for binding to an antibody for the hydrophobic drug is dependent on considerations such as, for example, the binding affinity of particular metabolites for the antibody for the hydrophobic drug. The above percentages are based on the assumption that the drug metabolites have approximately the same binding affinity for the antibody for the hydrophobic drug as the hydrophobic drug itself. Otherwise, the above percentages should be adjusted based on the actual binding affinity of the hydrophobic drug metabolites.

In some embodiments the releasing agent is an analog, including structural analogs, of the hydrophobic drug. A hydrophobic drug analog is a modified drug that can displace the analogous hydrophobic drug from a binding protein but does not compete to any substantial degree for a receptor such as an antibody for the hydrophobic drug. The modification provides means to join a hydrophobic drug analog to another molecule. The hydrophobic drug analog will usually differ from the hydrophobic drug by more than replacement of a hydrogen with a bond which links the drug analog to a hub or label, but need not. The hydrophobic drug analog may be, for example, the hydrophobic drug conjugated to another molecule through a linking group, and so forth. For hydrophobic drugs that comprise a hydroxy or carboxylic acid functionality, the releasing agent may be an ester of the hydrophobic drug, which has a high binding affinity for endogenous binding proteins relative to the hydrophobic drug to be detected and which has no significant binding affinity for an antibody for the hydrophobic drug. For example, in a determination for sirolimus, an ester of sirolimus may be employed as the releasing agent so long as it meets the above requirements. A structural analog is a moiety that has the same or similar structural or spatial characteristics as the hydrophobic drug such that the structural analog accomplishes the same or similar result as the analog of the hydrophobic drug. The structural analog may be, for example, another compound that is related to the hydrophobic drug. For example, in a determination for sirolimus, an ester of tacrolimus may be employed as the releasing agent. The ester may be, for example, a carbamate, a carbonate, an ester of a $C_1$ to $C_6$ carboxylic acid, and the like. See, for example, U.S. Pat. No. 7,186,518, the relevant disclosure of which is incorporated herein by reference. Other examples of releasing agents include [$Thr_2$, $Leu_5$, $D-Hiv_8$, $Leu_{10}$]-cyclosporin A for cyclosporin A, FK506 for sirolimus, sirolimus for FK506, and the like. See, for example, U.S. Pat. No. 6,187,547, the relevant disclosure of which is incorporated herein by reference.

The concentration of the releasing agent in the medium is that sufficient to achieve the desired result of displacing the hydrophobic drug, and in many instances the metabolites of the hydrophobic drug, from endogenous binding moieties to render the drug and metabolites accessible for binding to an antibody for the drug as discussed above. The amount or concentration of the releasing agent employed depends on the nature of the sample, the nature of the hydrophobic drug, the nature of the drug metabolites, the nature of other reagent components, the reaction conditions and the like. In some embodiments the amount of the releasing agent is about 0.000001% to about 0.5%, about 0.0001% to about 0.4%, about 0.001% to about 0.3%, about 0.01% to about 0.2%, about 0.1% to about 0.3%, about 0.2% to about 0.5%, about 0.1% to about 0.2%, and so forth (percent is weight/volume).

Selective Solubility Agent

The selective solubility agent promotes equalization of the bioavailability of the hydrophobic drug and that of the metabolites in the medium. The nature of the selective solubility agent is such as to provide a quasi-hydrophobic milieu to dissolve drug and/or drug metabolites, which are released from endogenous binding moieties by the releasing agent. By using the selective solubility agent, the drug and metabolite are made similarly accessible to the assay antibody, resulting in reduction of metabolite cross-reactivity that would be otherwise higher due to its lower protein binding and higher solubility in a pure aqueous solution compared to the parent drug. The presence of a selective solubility agent in accordance with the embodiments herein ensures that both the released drug and metabolites are substantially equally dissolved in the pretreatment medium and/or in the assay medium. In some embodiments the selective solubility agent enhances the bioavailability of a hydrophobic antibody that is employed in an assay.

The selective solubility agent comprises a water miscible, non-volatile organic solvent and is usually a liquid at room temperature (about 18° C. to about 23° C.). The selective solubility agent should comprise a hydrophilic or polar region in the molecule for it to be miscible with water and a hydrophobic or non-polar region so that it can dissolve hydrophobic drugs and, therefore, has a hydrophobic drug-dissolving capability. Nevertheless, the overall polarity is such that the organic solvent is miscible with water. The organic solvent is miscible with water when it is capable of dissolving in water in all proportions at a temperature of about 1 to about 50° C. The organic solvents that may be used as the selective solubility agent have unlimited solubility in an aqueous medium.

As mentioned above, the selective solubility agent, when added to the pretreatment medium or assay medium, assists in dissolving hydrophobic drugs in the medium. The extent to which a hydrophobic drug dissolves in a medium that contains the selective solubility agent versus the same medium in the absence of the selective solubility agent is greater than about 80%, or greater than about 85%, or greater than about 90%, or greater than about 95%, or about 100% or greater. For example, if 2 ng/mL of hydrophobic drug dissolved in a medium without the selective solubility agent and 4 ng/mL of hydrophobic drug dissolved in the same medium that contained the selective solubility in the appropriate range, the increase would be 100%.

The term "nonvolatile" means that the organic solvent has a vapor pressure as low as or lower than pure water at a given temperature, and, after combination with water in a percentage in accordance with the present methods, the resulting medium has a vapor pressure, at a given temperature, as low as or lower than that of pure water. For example, the vapor pressure of DMSO at 8° C. is 21.7 Pa and the vapor pressure of water at 8° C. is 1044 Pa; the vapor pressure of 15% DMSO in water is 978 Pa, which is lower than that of the pure water. On the other hand, ethanol, for example, would not be a suitable selective solubility agent in accordance with the present methods because its vapor pressure at 8° C. is 2754 Pa, much higher than that of pure water. The vapor pressure of a mixture of 10% ethanol in water has a vapor pressure of 1115 Pa, which is higher than that of pure water.

In addition to carbon and hydrogen, the organic solvent employed as the selective solubility agent may contain one or more of oxygen, sulfur, nitrogen, phosphorus, which may be present in various combinations to form functionalities such as, for example, hydroxyl, amine, amide, thiol, sulfoxide, sulfone, phosphate, phosphite, carboxylic acid ester, ether, and so forth. In some embodiments the selective solubility agent contains 2 carbon atoms, or 3 carbon atoms, or 4 carbon atoms, or 5 carbon atoms, or 6 carbon atoms as well as one or more of the above functionalities. Embodiments of the selective solubility agent include, by way of illustration and not limitation, $C_2$, or $C_3$, or $C_4$, or $C_5$, or $C_6$ polyols comprising 2 hydroxy groups or 3 hydroxy groups such as, for example, ethylene glycol, propylene glycol, glycerol, and the like, $C_2$, or $C_3$, or $C_4$, or $C_5$, or $C_6$ sulfoxides such as, for example, dimethyl sulfoxide, diethyl sulfoxide, and so forth, $C_2$, or $C_3$, or $C_4$, or $C_5$, or $C_6$ sulfones such as, for example, dimethyl sulfone, diethyl sulfone, and so forth, $C_2$, or $C_3$, or $C_4$, or $C_5$, or $C_6$ amides such as, for example, formamides, e.g., dimethyl formamide, diethyl formamide, N-methylpyrrolidone, tetramethyl urea, dimethylacetamide, and so forth, $C_2$ to $C_6$ mono-, di- and tri-ethers of a polyol comprising 2 hydroxy groups or 3 hydroxy groups such as, for example, 1-methoxy-2-propanol, 1,2-dimethoxy propanol, and so forth and $C_2$ to $C_6$ mono-, di- and tri-esters of a polyol comprising 2 hydroxy groups or 3 hydroxy groups such as, for example, 2-hydroxypropyl acetate, bis(2-methoxyethyl)ether (diglyme), and so forth. The selective solubility agent may be a single organic solvent or a combination of organic solvents having the aforementioned properties.

The concentration of the selective solubility agent in the medium is sufficient to achieve selective enhancement of the bioavailability of the hydrophobic drug, over that of the metabolites, in the medium. Selective enhancement of the bioavailability of the hydrophobic drug over that of its metabolites is achieved when the amount of hydrophobic drug that is detectable is increased over that obtained in the absence of the selective solubility agent by at least about 50%, by at least about 75%, by at least about 90%, by at least about 100%, by at least about 125%, by at least about 150%, by at least about 175%, by at least about 200%, by at least about 225%, by at least about 250%, by at least about 275%, by at least about 300%, by at least about 325%, by at least about 350%, by at least about 375%, by at least about 400%, and so forth. In other words, selective enhancement of the bioavailability of the hydrophobic drug over that of its metabolites is achieved when the amount of hydrophobic drug that is detectable is increased over that obtained in the absence of the selective solubility agent by about 0.5 to about 4 times, or about 0.75 to about 4 times, or about 1 to about 4 times, or about 0.5 to about 3.5 times, or about 0.5 to about 3 times, or about 0.5 to about 2.5 times, or about 0.5 to about 2 times, or about 0.75 to about 3.5 times, or about 0.75 to about 3 times, or about 0.75 to about 2.5 times, or about 0.75 to about 2 times, or about 1 to about 3.5 times, or about 1 to about 3 times, or about 1 to about 2.5 times, or about 1 to about 2 times, and so forth.

The amount or concentration of selective solubility agent employed depends on the nature of the sample, the nature of the hydrophobic drug, the nature of the organic solvent, the nature of other reagent components, the reaction conditions, whether the medium is a pretreatment medium or an assay medium, and the like. In some embodiments the amount of the selective solubility agent in a pretreatment medium is about 10% to about 30%, about 11% to about 25%, about 12% to about 20%, about 13% to about 19%, about 14% to about 18%, about 15% to about 17%, about 15% to about 25%, about 16% to about 24%, about 17% to about 23%, about 18% to about 22%, about 19% to about 21%, about 15% to about 20%, about 16% to about 19%, and so forth (volume to volume). In some embodiments the amount of the selective solubility agent in an assay medium is about 1.0% to about 10%, about 2.0% to about 9.0%, about 2.1% to about 8.0%, about 2.2% to about 7.0%, about 2.3% to about 6.0%, about 2.4% to about 5%, about 2.5% to about 4.5%, about 3.0% to about 6.0%, about 3.1% to about 5.0%, about 3.2% to about 4.9%, about 3.3% to about 4.8%, about 3.4% to about 4.7%, about 3.5% to about 4.5%, and so forth (volume to volume).

Pretreatment of Sample

The sample, a hemolytic agent (if employed), the releasing agent and the selective solubility agent are combined in a medium, which, as mentioned above, is usually an aqueous medium and is referred to herein as a pretreatment medium. All of the above may be combined simultaneously in the medium or one or more of the above reagents may be added sequentially in concentrations as discussed above. The medium may also comprise one or more preservatives as are known in the art such as, for example, sodium azide, neomycin sulfate, PROCLIN® 300, Streptomycin, and the like. The pH for the medium will usually be in the range of about 4 to about 11, more usually in the range of about 5 to about 10, and preferably in the range of about 6.5 to about 9.5.

Various buffers may be used to achieve the desired pH and maintain the pH during the incubation period. Illustrative buffers include borate, phosphate, carbonate, tris, barbital, PIPES, HEPES, MES, ACES, MOPS, BICINE, and the like. The medium may also comprise agents for preventing the formation of blood clots. Such agents are well known in the art and include, for example, EDTA, EGTA, citrate, heparin, and the like. Various ancillary materials may be employed in the above methods. For example, in addition to buffers and preservatives, the medium may comprise stabilizers for the medium and for the reagents employed. All of the above materials are present in a concentration or amount sufficient to achieve the desired effect or function.

The medium is incubated under conditions for hemolyzing cells in the sample, for releasing the hydrophobic drug and its metabolites from endogenous binding moieties and for enhancing the bioavailability of the hydrophobic drug. The incubation period may be about 1 second to about 60 minutes, or about 1 second to about 6 minutes, or about 1 second to about 5 minutes, or about 1 second to about 3 minutes, or about 1 second to about 2 minutes, or about 1 second to about 1 minute, or about 1 second to about 30 seconds, or about 1 second to about 20 seconds, or about 1 second to about 10 seconds, or about 5 seconds to about 60 minutes, or about 5 seconds to about 6 minutes, or about 5 seconds to about 5 minutes, or about 5 seconds to about 3 minutes, or about 5 seconds to about 2 minutes, or about 5 seconds to about 1 minute, or about 5 seconds to about 30 seconds, or about 5 seconds to about 20 seconds, or about 5 seconds to about 10 seconds, or about 10 seconds to about 60 minutes, or about 10 seconds to about 6 minutes, or about 10 seconds to about 5 minutes, or about 10 seconds to about 3 minutes, or about 10 seconds to about 2 minutes, or about 10 seconds to about 1 minute, or about 10 seconds to about 30 seconds, or about 10 seconds to about 20 seconds, or about 20 seconds to about 60 minutes, or about 20 seconds to about 6 minutes, or about 20 seconds to about 5 minutes, or about 20 seconds to about 3 minutes, or about 20 seconds to about 2 minutes, or about 20 seconds to about 1 minute, or about 20 seconds to about 30 seconds, or about 30 seconds to about 60 minutes, or about 30 seconds to about 6 minutes, or about 30 seconds to about 5 minutes, or about 30 seconds to about 3 minutes, or about 30 seconds to about 2 minutes, or about 30 seconds to about 1 minute, or about 1 minute to about 30 minutes, or about 1 minute to about 20 minutes, or about 1 minute to about 10 minutes, or the like.

The temperature during the incubation is usually about 10° C. to about 45° C., or about 10° C. to about 35° C., or about 10° C. to about 25° C., or about 15° C. to about 45° C., or about 15° C. to about 35° C., or about 15° C. to about 25° C., or about 20° C. to about 45° C., or about 20° C. to about 35° C., or about 20° C. to about 25° C., or the like.

General Description of Assays for a Hydrophobic Drug

Following the above incubation period, reagents for determining the presence and/or amount of the hydrophobic drug in the sample are added to the medium. The nature of the reagents is dependent on the particular type of assay to be performed. In general, the assay is a method for the determination or measuring of the presence and/or amount of a hydrophobic analyte. Various assay methods are discussed below by way of illustration and not limitation.

In many embodiments the reagents comprise at least one antibody for the hydrophobic drug. By the phrase "antibody for the hydrophobic drug" is meant an antibody that binds specifically to the hydrophobic drug and does not bind to any significant degree to other substances that would distort the analysis for the hydrophobic drug.

Antibodies specific for a hydrophobic drug for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1-24 (1975); Broughton and Strong, Clin. Chem. 22: 726-732 (1976); and Playfair, et al., Br. Med. Bull. 30: 24-31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites.

As discussed above, an antibody selected for use in an immunoassay for a hydrophobic drug, for example, should specifically and preferentially bind the hydrophobic drug and its pharmaceutically active metabolites over other ligands such as other metabolites or related drugs. For example, an antibody for tacrolimus should specifically and preferentially bind tacrolimus over, e.g., rapamycin. In general, an antibody should be capable of distinguishing between one hydrophobic drug relative to a second hydrophobic drug. At least about 5-fold, at least about 10-fold, or at least about 20-fold, of the first hydrophobic drug will be bound to the antibody if the antibody is combined with a sample containing the hydrophobic drug. While the binding also depends on relative concentration of the hydrophobic drug, the binding will be higher for the first hydrophobic drug if the binding constant for the first hydrophobic drug is greater than the binding constant for the second hydrophobic drug, at least about 10-fold higher or at least about 50-fold higher and up to 1000-fold or higher.

Other reagents are included in the assay medium depending on the nature of the assay to be conducted. Such assays usually involve reactions between binding partners such as a hydrophobic drug analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

Many types of immunoassays may be employed in the present methods to determine the presence and/or amount of a hydrophobic drug analyte in a sample suspected of containing such analytes. The immunoassays may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include enzyme immunoassays, fluorescence polarization immunoassays, radioimmunoassay, inhibition assay, induced luminescence, fluorescent oxygen channeling assay, and so forth.

In many of the assays discussed herein, a label is employed; the label is usually part of a signal producing system ("sps").

The nature of the label is dependent on the particular assay format. An sps usually includes one or more components, at least one component being a detectable label, which generates a detectable signal that relates to the amount of bound and/or unbound label, i.e. the amount of label bound or not bound to the hydrophobic drug being detected or to an agent that reflects the amount of the hydrophobic drug to be detected. The label is any molecule that produces or can be induced to produce a signal, and may be, for example, a fluorescer, radiolabel, enzyme, chemiluminescer or photosensitizer. Thus, the signal is detected and/or measured by detecting enzyme activity, luminescence, light absorbance or radioactivity, and so forth, as the case may be.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

The label or other sps members can be bound to a support. A hydrophobic drug derivative or analog may be bound to a solid support in any manner known in the art, provided only that the binding does not substantially interfere with the analogs ability to bind with an antibody. In some embodiments, the hydrophobic drug derivative or analog may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the hydrophobic drug. Other methods of binding the hydrophobic drug derivatives are also possible. For instance, a solid support may have a coating of a binder for a small molecule such as, for example, avidin, an antibody, etc., and a small molecule such as, e.g., biotin, hapten, etc., can be bound to the hydrophobic drug derivative or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, *J. Biol. Chem.*, 245:3059 (1970).

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, paper, etc., fiber, and the like. Depending on the type of assay, the support may or may not be suspendable in the medium in which it is employed. Examples of suspendable supports are polymeric materials such as latex, lipid bilayers or liposomes, oil droplets, cells and hydrogels, magnetic particles, and the like. Other support compositions include polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

The support may be a particle. The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chromium dioxide (chrome) particles or latex particles.

The polymer particles can be formed of addition or condensation polymers. The particles will be readily dispersible in an aqueous medium and can be adsorptive or functionalizable so as to permit conjugation to a hydrophobic drug analog, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The label and/or other sps member may be bound to an sbp member or another molecule. For example, the label can be bound covalently to an sbp member such as, for example, an antibody; a receptor for an antibody, a receptor that is capable of binding to a small molecule conjugated to an antibody, or a ligand analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Enzymes of particular interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

With label proteins such as, for example, enzymes, the molecular weight range will be from about 10,000 to about 600,000, or from about 10,000 to about 300,000 molecular weight. There is usually at least about 1 hydrophobic drug analog per about 200,000 molecular weight, or at least about 1 per about 150,000 molecular weight, or at least about 1 per about 100,000 molecular weight, or at least about 1 per about 50,000 molecular weight, and so forth. In the case of enzymes, the number of hydrophobic drug analog groups is usually from 1 to about 20, about 2 to about 15, about 3 to about 12, or about 6 to about 10.

The term "non-poly(amino acid) labels" includes those labels that are not proteins (e.g., enzymes). The non-poly (amino acid) label is capable of being detected directly or is detectable through a specific binding reaction that produces a detectable signal. The non-poly(amino acid) labels include, for example, radioisotopes, luminescent compounds, supports, e.g., particles, plates, beads, etc., polynucleotides, and the like. More particularly, the non-poly(amino acid) label can be isotopic or non-isotopic, usually non-isotopic, and can be a polynucleotide coding for a catalyst, promoter, dye, coenzyme, enzyme substrate, radioactive group, a small organic molecule (including, e.g., biotin, fluorescent molecules, chemiluminescent molecules, and the like), amplifiable polynucleotide sequence, a support such as, for example, a particle such as latex or carbon particle or chromium dioxide (chrome) particle or the like, metal sol, crystallite, liposome, cell, etc., which may or may not be further labeled with a dye, catalyst or other detectable group, and the like.

One general group of immunoassays that may be employed includes immunoassays using a limited concentration of antibody. Another group of immunoassays involves the use of an excess of one or more of the principal reagents such as, for example, an excess of an antibody for the immunosuppressant drug. Another group of immunoassays are separation-free homogeneous assays in which the labeled reagents modulate the label signal upon hydrophobic drug-antibody binding reactions. Another group of assays includes labeled antibody reagent limited competitive assays for hydrophobic drug that avoid the use of problematic labeled haptens. In this type of assay, the solid phase immobilized hydrophobic drug analyte is present in a constant, limited amount. The partition of a label between the immobilized hydrophobic drug analyte and free hydrophobic drug analyte depends on the concentration of analyte in the sample.

The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of an antibody-immobilized surface upon the binding of a hydrophobic drug. Such assays include, for example, optical immunosensor assays, acoustic immunosensor assays, semiconductor immunosensor assays, electrochemical transducer immunosensor assays, potentiometric immunosensor assays, amperometric electrode assays, and the like.

In one embodiment the assay is an induced luminescence immunoassay, which is described in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member, for example, an antibody for the hydrophobic drug that is capable of binding to the hydrophobic drug analyte to form a complex, or to a second sbp member to form a complex, in relation to the presence of the hydrophobic drug analyte. If the hydrophobic drug analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of hydrophobic drug analyte present.

By way of further illustration, chemiluminescent particles are employed, which comprise the chemiluminescent compound associated therewith such as by incorporation therein or attachment thereto. An sbp member that binds to the hydrophobic drug analyte, such as, for example, an antibody for a hydrophobic drug, is bound to a polysaccharide coating the particles. A second sbp member that binds to the hydrophobic drug analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with a sample suspected of containing a hydrophobic drug analyte and the photosensitizer particles. The reaction medium is incubated to allow the particles to bind to the hydrophobic drug analyte by virtue of the binding of the sbp members to the hydrophobic drug analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the hydrophobic drug analyte, it is activated by singlet oxygen and emits luminescence. The medium is then examined for the presence and/or the amount of luminescence or light emitted, the presence thereof being related to the presence and/or amount of the hydrophobic drug analyte.

Another particular example of an assay that may be employed for the determination of a hydrophobic drug analyte is discussed in U.S. Pat. No. 5,616,719 (Davalian, et al.), which describes fluorescent oxygen channeling immunoassays.

In some embodiments multi-analyte immunoassays may be utilized where the hydrophobic drug analyte may be the subject of detection along with one or more other analytes such as other drugs and the like. Such multi-analyte systems are described, for example, in Loor, et al., J. Anal. Toxicol. 12: 299 (1988).

The assays discussed above are normally carried out in an aqueous buffered medium at a moderate pH, generally that which provides optimum assay sensitivity. The pH for the assay medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the determination. Illustrative buffers include borate, phosphate, carbonate, tris, barbital and the like. The particular buffer employed is not critical, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; quaternary ammonium salts; polyanions such as dextran sulfate; binding enhancers, or the like.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 24 hours, or about 1 second to about 6 hours, or about 2 seconds to about 1 hour, or about 1 to about 15 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., or from about 15 to about 40° C.

The concentration of analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of hydrophobic drug analyte present in the sample), the particular detection technique and the concentration of the analyte normally determine the concentrations of the various reagents.

The concentrations of the various reagents in the assay medium will generally be determined by the concentration range of interest of the hydrophobic drug analyte, the nature of the assay, and the like. However, the final concentration of each of the reagents is normally determined empirically to optimize the sensitivity of the assay over the range. That is, a variation in concentration of hydrophobic drug analyte that is of significance should provide an accurately measurable signal difference. Considerations such as the nature of the signal producing system and the nature of the analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above.

Examination Step

In a next step of the method in accordance with the present disclosure, the medium is examined for the presence of a complex comprising the hydrophobic drug and the antibody for the hydrophobic drug. The presence and/or amount of the complex indicates the presence and/or amount of the hydrophobic drug in the sample.

The phrase "measuring the amount of a hydrophobic drug analyte" refers to the quantitative, semiquantitative and qualitative determination of the hydrophobic drug analyte. Methods that are quantitative, semiquantitative and qualitative, as well as all other methods for determining the hydrophobic drug analyte, are considered to be methods of measuring the amount of the hydrophobic drug analyte. For example, a method, which merely detects the presence or absence of the hydrophobic drug analyte in a sample suspected of containing the hydrophobic drug analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the hydrophobic drug in the sample. The particular mode of detection depends on the nature of the sps. As discussed above, there are numerous methods by which a label of an sps can produce a signal detectable by external means, desirably by visual examination, and include, for example, electromagnetic radiation, electrochemistry, heat, radioactivity detection, chemical reagents and so forth.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems, addition of a substrate and/or a cofactor may be necessary.

The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the hydrophobic drug compound present in a sample. Temperatures during measurements generally range from about 10° to about 70° C., or from about 20° to about 45° C., or about 20° to about 25° C. In one approach standard curves are formed using known concentrations of the analytes to be screened. As discussed above, calibrators and other controls may also be used.

Specific Embodiments of Assays

The following examples describe specific embodiments of the invention by way of illustration and not limitation and are intended merely to describe, and not to limit, the scope of the invention.

In a homogeneous assay after all of the reagents have been combined, the signal is determined and related to the amount of analyte in the sample. For example, in an EMIT® assay for a hydrophobic drug, a sample suspected of containing the hydrophobic drug is combined in an aqueous medium either simultaneously or sequentially with an enzyme conjugate of the hydrophobic drug, i.e., an analog for the hydrophobic drug, and antibody capable of recognizing the hydrophobic drug. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The hydrophobic drug analyte and the moieties of the enzyme conjugate compete for binding sites on the antibody. The enzyme activity in the medium is then determined, usually by spectrophotometric means, and is compared to the enzyme activity determined when calibrators or reference samples are tested in which a known amount of the hydrophobic drug is present. Typically, the calibrators are tested in a manner similar to the testing of the sample suspected of containing the hydrophobic drug analytes. The calibrators typically contain differing, but known, concentrations of the hydrophobic drug analyte to be determined. Preferably, the concentration ranges present in the calibrators span the range of suspected hydrophobic drug analyte concentrations in unknown samples.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using antibodies for the hydrophobic drug and using procedures as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, which disclosure is incorporated herein by reference. In one type of competitive assay, a support, as discussed herein, having antibodies for the hydrophobic drug bound thereto is contacted with a medium containing the sample and appropriate enzyme conjugates of the hydrophobic drug. After separating the support and the medium, the enzyme activity of the support or the medium is determined by conventional techniques and related to the presence and/or amount of the hydrophobic drug in the sample.

In certain embodiments a second enzyme may be employed in addition to the enzyme of the enzyme conjugate. The enzymes of the pair of enzymes are related in that a product of the first enzyme serves as a substrate for the second enzyme.

Another embodiment of an assay format is a capture assay. In this assay format, the antibody for the hydrophobic drug is covalently bound to a magnetic particle. The sample is incubated with these particles to allow the hydrophobic drug in the sample to bind to the antibodies for the hydrophobic drug. Subsequently, an enzyme that has the hydrophobic drug or a derivative of the hydrophobic drug covalently attached is incubated with the magnetic particles. After washing, the amount of enzyme that is bound to the magnetic particles is measured and is inversely related to the presence and/or amount of the hydrophobic drug in the sample.

The following specific assay descriptions are by way of illustration of, and not as a limitation on, the scope of the present invention. Selection of sirolimus as the hydrophobic drug is also by way of illustration and not limitation as the present invention has general application to detection of hydrophobic drugs in general and immunosuppressant drugs in particular.

In one embodiment, the test sample or a sirolimus standard is mixed with a sirolimus conjugate, i.e., for example, an analog of sirolimus that is attached to biotin. The sirolimus of the test sample and the analog of sirolimus are allowed to compete for binding to the antibody for the sirolimus, which is capable of binding to sirolimus or the analog of sirolimus. After rinsing with an appropriate wash buffer, a detection molecule consisting of streptavidin or avidin conjugated to an enzyme, florescent or chemiluminescent molecule or radioactive moiety can be added to the medium, which is then examined for the presence and/or amount of signal. The presence and/or amount of signal is related to the presence and/or amount of sirolimus.

In one embodiment the assay employed is an induced luminescence assay as described above. The reagents include two latex bead reagents and a biotinylated anti-sirolimus mouse monoclonal antibody. The first bead reagent is coated with sirolimus or a sirolimus analog and contains chemiluminescent dye. The second bead reagent is coated with streptavidin and contains a photosensitizer dye. In a first step, sample suspected of containing sirolimus is incubated with biotinylated antibody for sirolimus, which allows sirolimus from the sample to saturate a fraction of the biotinylated antibody that is directly related to the sirolimus concentration. In a second step, the first bead reagent is added and leads to the formation of bead/biotinylated antibody immunocomplexes with the non-saturated fraction of the biotinylated antibody. The second bead reagent is then added and binds to the biotin to form bead pair immunocomplexes. When illuminated by light at 680 nm, the second bead reagent converts dissolved oxygen in the reaction solution into the more energetic singlet oxygen form. In the bead pairs, the singlet oxygen diffuses into the first bead reagent thereby triggering a chemiluminescent reaction. The resulting chemiluminescent signal is measured at 612 nm and is an inverse function of the concentration of sirolimus in the sample. The amount of this signal is related to the presence and or amount of sirolimus in the sample.

A specific example of another assay format is ACMIA (Affinity Chromium dioxide Mediated Immuno Assay). For the ACMIA assay format, chrome particles, which are coated with sirolimus or a sirolimus analog, are employed as a first component. A second component is an antibody for sirolimus. This antibody, crosslinked to a reporter enzyme (for example, beta-galactosidase), is added to a reaction vessel in an excess amount, i.e., an amount greater than that required to bind all of the analyte that might be present in a sample. The antibody-enzyme conjugate is mixed with a sample suspected of containing sirolimus to allow the sirolimus analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the presence and/or amount of sirolimus in the sample.

In a sandwich assay format, a first reagent comprising chrome particles coated with anti-sirolimus antibodies and a second reagent comprising a second antibody (or binding protein) for the first antibody conjugated to a reporter enzyme are employed. In this format, the sample suspected of containing sirolimus is incubated with the chrome particles so that all of the sirolimus, if present in the sample, becomes bound to the chrome particles. The chrome particles are washed, using a magnet to separate the bound analyte from the supernatant. Then, the second reagent, i.e., antibody (or binding protein) conjugated to a reporter enzyme, is incubated with the chrome particles to form a "sandwich". After washing, the amount of enzyme that is bound to the chrome is measured and is related to the presence and/or amount of sirolimus in the sample.

Another assay format is EMIT® (Enzyme-Mediated Immunoassay Technology). In this assay format, an enzyme conjugate is formed such as, for example, a conjugate of G-6-PDH and a sirolimus analog. An antibody for sirolimus is incubated with the enzyme-conjugate and a sample suspected of containing sirolimus. Antibody for sirolimus binds to the sirolimus analyte in the sample instead of binding to the enzyme conjugate, which reduces the amount of inhibition of the enzyme activity that might otherwise occur in the absence of sirolimus in the sample. In this way, samples with more sirolimus analyte will yield higher enzyme activity, and samples with no sirolimus analyte will have the maximum inhibition and the lowest enzyme activity. The amount of reduction of inhibition of enzyme activity is related to the amount of sirolimus in the sample.

The reagents for conducting a particular assay may be present in a kit useful for conveniently performing an assay for the determination of a hydrophobic drug analyte. In one embodiment a kit comprises in packaged combination an antibody for a hydrophobic drug analyte and other reagents for performing an assay, the nature of which depend upon the particular assay format. The reagents may each be in separate containers or various reagents can be combined in one or more containers depending on the cross-reactivity and stability of the reagents. The kit can further include other separately packaged reagents for conducting an assay such as additional sbp members, ancillary reagents such as an ancillary enzyme substrate, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

Other Embodiments

One embodiment of the present invention is a method for pretreating a sample suspected of containing a hydrophobic drug for conducting an assay method for detecting the hydrophobic drug. A combination is provided in a medium. The combination comprises (i) the sample, (ii) a releasing agent for releasing the hydrophobic drug and its metabolites from endogenous binding moieties, and (iii) a selective solubility agent that provides for substantially equal solubility of the hydrophobic drug and its metabolites in the medium. The selective solubility agent comprises a water miscible, non-volatile organic solvent and is present in the medium in a concentration sufficient to provide for substantially equal solubility of the hydrophobic drug and its metabolites in the medium. The medium is incubated under conditions for releasing the hydrophobic drug and its metabolites from endogenous binding moieties.

Another embodiment of the present invention is a method for determining a hydrophobic drug in a sample suspected of containing a hydrophobic drug. A combination is provided in a medium. The combination comprises (i) the sample, (ii) a releasing agent for releasing the hydrophobic drug and its metabolites from endogenous binding moieties, and (iii) a selective solubility agent that provides for substantially equal solubility of the hydrophobic drug and its metabolites in the medium, wherein the selective solubility agent comprises a water miscible, non-volatile organic solvent and wherein the concentration of the selective solubility agent in the medium is sufficient to provide for substantially equal solubility of the hydrophobic drug and its metabolites in the medium. The combination in the medium further comprises a hemolytic agent. The medium is incubated under conditions for hemolyzing cells in the sample and for releasing the hydrophobic drug and its metabolites from endogenous binding moieties. To the medium is added reagents for determining the presence and/or amount of the hydrophobic drug in the sample wherein the reagents comprise at least one antibody for the hydrophobic drug. The medium is examined for the presence of a complex comprising the hydrophobic drug and the antibody for the hydrophobic drug, the presence and/or amount of the complex indicating the presence and/or amount of the hydrophobic drug in the sample.

Another embodiment of the present invention is a method for determining an immunosuppressant drug in a sample suspected of containing an immunosuppressant drug. A combination is formed in a medium wherein the combination comprises the sample, a releasing agent for releasing the immunosuppressant drug and its metabolites from endogenous binding moieties and a selective solubility agent for the immunosuppressant drug and its metabolites. The selective solubility agent comprises a water miscible, non-volatile organic solvent. The concentration of the selective solubility agent in the medium is sufficient to provide for substantially equal solubility of the immunosuppressant drug and its metabolites in the medium. The medium is incubated under conditions for releasing the immunosuppressant drug and its metabolites from endogenous binding moieties. To the medium is added (i) a reagent comprising (I) an antibody for the immunosuppressant drug and (II) an enzyme and (ii) magnetic particles comprising the immunosuppressant drug or an analog thereof. The medium is examined for the presence of a complex comprising the immunosuppressant drug and the antibody for the immunosuppressant drug, the presence and/or amount of the complex indicating the presence and/or amount of the immunosuppressant drug in the sample.

Another embodiment of the present invention is a method for determining an immunosuppressant drug in a sample suspected of containing an immunosuppressant drug. A combination is formed in a medium wherein the combination comprises the sample, a releasing agent for releasing the immunosuppressant drug and its metabolites from endogenous binding moieties and a selective solubility agent for the immunosuppressant drug and its metabolites. The selective solubility agent comprises a water miscible, non-volatile organic solvent and the concentration of the selective solubility agent in the medium is sufficient to provide for substantially equal solubility of the immunosuppressant drug and its metabolites in the medium. The medium is incubated under conditions to provide for substantially equal solubility of the immunosuppressant drug and its metabolites in the medium. To the medium is added (i) a photosensitizer associated with a first particle and being capable of generating singlet oxygen, and (ii) a chemiluminescent composition activatable by singlet oxygen and associated with a second particle, wherein an antibody for the immunosuppressant drug is associated with the first particle or the second particle or both. The combination is subjected to conditions for binding of the antibody to the immunosuppressant drug, if present. The photosensitizer is irradiated with light and the amount of luminescence generated by the chemiluminescent composition is detected. The amount of luminescence is related to the amount of the immunosuppressant drug in the sample.

Alternatively, in the above embodiment, one of the first particle or the second particle comprises the antibody and the other particle comprises a drug analog for the immunosuppressant drug. The combination is subjected to conditions for competition of the drug analog coated particles and the immunosuppressant drug, if present, to the antibody for the drug. Alternatively, in the above embodiment, the first particle or the second particle comprises streptavidin, which combines with a biotinylated analog for the immunosuppressant drug in the medium. The combination is subjected to conditions for competition of biotinylated drug analog and the immunosuppressant drug for the antibody for the drug. In either of the above alternative embodiments, the photosensitizer is irradiated with light and the amount of luminescence generated by the chemiluminescent composition is detected. The amount of luminescence is related to the amount of the immunosuppressant drug in the sample.

The following examples further describe the specific embodiments of the invention by way of illustration and not limitation and are intended to describe and not to limit the scope of the invention. Parts and percentages disclosed herein are by volume unless otherwise indicated.

EXAMPLES

Materials

All chemicals were purchased from the Sigma-Aldrich Company (St. Louis Mo.) unless otherwise noted. Sirolimus powder and its metabolites except for 27,39-O-didesmethyl (or 32,41-O-didesmethyl) sirolimus were all obtained from Wyeth Pharmaceuticals. 27,39-O-didesmethyl (or 32,41-O-didesmethyl) sirolimus was obtained from Dr. Uwe Christains laboratory at Department of Anesthesiology, University of Colorado Health Sciences Center, Denver, Colo.

Testing was done using the DIMENSION® RxL analyzer, available from Dade Behring Inc., Newark Del. The instrument was employed using ACMIA immunoassay technology. The ACMIA assay method is disclosed in U.S. Pat. Nos. 7,186,518, 5,147,529, 5,128,103, 5,158,871, 4,661,408, 5,151,348, 5,302,532, 5,422,284, 5,447,870, 5,434,051, the disclosures of which are incorporated herein in their entirety). In the embodiment of the ACMIA method used herein and discussed in more detail below, competition between sirolimus analog on chrome particles and sirolimus (SIRO) in patient samples for antibody for sirolimus conjugated to an enzyme (conjugate) was utilized to determine the amount of sirolimus in the patient samples. Conjugate that binds to the sirolimus analog on chrome particles was removed by magnetic separation. The enzymatic activity from conjugate remaining in the supernatant is measured and is directly proportional to the amount of sirolimus in the patient sample. In the ACMIA assay format employed, the enzymatic activity observed when testing a sample containing no sirolimus was indicative of the amount of enzymatic activity that was not bound to active antibody (i.e., cannot bind sirolimus on chrome particles). The enzymatic activity observed when no chrome particle is present is indicative of the total amount of enzymatic activity in the conjugate. These values can be used to estimate the percent of enzymatic activity bound to active antibody.

Example 1

Automated Immunoassay for Hydrophobic Drugs with Varying Degrees of Metabolite Cross-Reactivity Utilizing a Non-Manual Pretreatment Preparation of Pretreatment Solution without FK-506 Carbamate (FKE)

This pretreatment solution was prepared to contain 6.8 mg/mL PIPES™ 1.5 sodium salt, 0.3 mg/mL EDTA Disodium, 1.0 mg/mL Saponin, 0.09% PLURONIC® 25R2, 0.2% Proclin 300, 0.024 mg/mL Neomycin sulfate and 0.99 mg/mL NaN$_3$, pH 6.5. No organic solvent was added in this solution. Preparation of Pretreatment Solution Containing 3.75 µg/mL FKE This pretreatment solution was prepared to contain 3.75 µg/mL of a FK-506 carbamate compound (or tacrolimus ester), 6.8 mg/mL PIPES™ 1.5 sodium salt, 0.3 mg/mL EDTA Disodium, 1.0 mg/mL Saponin, 0.09% PLURONIC® 25R2, 0.2% Proclin 300, 0.024 mg/mL Neomycin sulfate and 0.99 mg/mL NaN$_3$, pH 6.5. No organic solvent was added in this solution. The FKE concentration in the final reaction mixture was 0.86 µg/mL.

Preparation of Pretreatment Solution Containing 15 µg/mL FKE

This pretreatment solution was prepared to contain 15 µg/mL of a FK-506 carbamate compound (or tacrolimus ester), 6.8 mg/mL PIPES™ 1.5 sodium salt, 0.3 mg/mL EDTA Disodium, 1.0 mg/mL Saponin, 0.09% PLURONIC® 25R2, 0.2% Proclin 300, 0.024 mg/mL Neomycin sulfate and 0.99 mg/mL NaN$_3$, pH 6.5. No organic solvent was added in this solution. The FKE concentration in the final reaction mixture was 3.4 µg/mL.

Preparation of Pretreatment Solution Containing 10% Dimethyl Sulfoxide (DMSO)

This pretreatment solution was prepared by adding DMSO to a final concentration of 10% (v/v) into a buffer containing 6.8 mg/mL PIPES™ 1.5 sodium salt, 0.3 mg/mL EDTA Disodium, 1.0 mg/mL Saponin, 15 µg/mL of a FK-506 carbamate compound (or tacrolimus ester), 0.09% PLURONIC® 25R2, 0.2% Proclin 300, 0.024 mg/mL Neomycin sulfate and 0.99 mg/mL NaN$_3$, pH 6.5. The concentration of DMSO in the final reaction mixture was approximately 2.3%.

Preparation of Pretreatment Solution Containing 15% DMSO

This pretreatment solution was prepared by adding DMSO to a final concentration of 15% (v/v) into a buffer containing 6.8 mg/mL PIPES™ 1.5 sodium salt, 0.3 mg/mL EDTA Disodium, 1.0 mg/mL Saponin, 15 µg/mL of a FK-506 carbamate compound (or tacrolimus ester), 0.09% PLURONIC® 25R2, 0.2% Proclin 300, 0.024 mg/mL Neomycin sulfate and 0.99 mg/mL NaN$_3$, pH 6.5. The concentration of DMSO in the final reaction mixture was approximately 3.4%.

Preparation of Pretreatment Solution Containing 10% 1-Methoxy-2-Propanol

This pretreatment base solution was prepared by adding 1-methoxy-2-propanol (MP) to a final concentration of 10% (v/v) into a buffer containing 6.8 mg/mL PIPES 1.5 sodium salt, 0.3 mg/mL EDTA Disodium, 1.0 mg/mL Saponin, 15 µg/mL of a FK-506 carbamate compound (or tacrolimus ester), 0.2% Proclin 300, 0.024 mg/mL Neomycin sulfate and 0.99 mg/mL NaN$_3$, pH 6.5. The concentration of MP in the final ACMIA reaction mixture was approximately 2.3%.

Table 1 shows the composition of the pretreatment reagent for use in pretreating a sample containing sirolimus (AI=as indicated).

TABLE 1

Composition of the pretreatment reagent for the sirolimus ACMIA assay

| Name | Qty. (per mL) | Function |
| --- | --- | --- |
| FK506 Ester | 15 µg | dissociates Sirolimus from binding protein |
| DMSO or MP | AI | dissolve drug and metabolites |
| SesquiNa PIPES | 6.8 mg | buffer |
| EDTA Disodium | 0.3 mg | preventing clot-formation |
| Saponin | 1.0 mg | blood cell lysis |
| Pluronic | 0.9 µL | |
| Proclin 300 | 2 µL | preservative |
| Neomycin Sulfate | 0.024 mg | preservative |
| NaN3 | 0.99 mg | preservative, matrix |

Preparation of Anti-Tacrolimus Antibody-β-Galactosidase Conjugate

Monoclonal anti-sirolimus antibody (Wyeth Pharmaceuticals, Cambridge Mass.) was conjugated to β-galactosidase using a standard heterobifunctional SMCC (succinimidyl trans-4-(N-maleimidylmethyl)cyclohexane-1-carboxylate) linker according to known techniques. The antibody conjugate solution contained approximately 7.5 μg/mL anti-sirolimus antibody-β-galactosidase conjugate, 30 mg/mL protease free bovine serum albumin, 0.126 mg/mL $MgCl_2$, 0.03 mL/mL of Ethylene glycol, 35.14 mg/mL PIPES 1.5 sodium salt, 50 mg/mL NaCl and beta-gal mutein (inactivated beta-galactosidase), pH 6.5.

Magnetic Chrome Particle Preparation

Sirolimus chrome particles (immunoassay solid phase) were prepared by conjugating sirolimus-C26- or -C32-CMO conjugate to DA10-Dexal-Chromium Dioxide particles using N-hydroxysuccinimide (NHS) ester and 1-ethyl-3-(3-dimethylaminopropyl)carbodiimide (EDAC) chemistry. See, for example, U.S. Pat. No. 6,231,982, the relevant disclosure of which is incorporated herein by reference. The sirolimus chrome particles are then made into sirolimus chrome particle tablets. Each sirolimus tablet contains approximately 2 mg sirolimus chrome particle slurry, 30.4 mg trehalose dihydrate and 3.6 mg CARBOWAX® 100 μm.

Sirolimus Assay

The principle and operation of the ACMIA assay for sirolimus were as follows: pretreatment reagent without FKE or with FKE containing organic solvent as the selective solubility agent was added to a reaction vessel on the DIMENSION® RxL analyzer. Next, 18 μL of whole blood containing sirolimus or its metabolites was added. The whole blood was sampled from a standard cup by first mixing the blood with the ultrasonic sample probe. The mixing of whole blood sample with the pretreatment solution ensured the hemolysis of the whole blood and the displacement of the protein bound sirolimus molecules from their binding sites when the tacrolimus carbamate molecules were present. Anti-sirolimus antibody-β-galactosidase conjugate (50 μL) was added next and was allowed to react with sirolimus in the sample. The chrome particles with immobilized sirolimus-CMO-DA10-Dexal were added (50 μL) and were allowed to bind the un-bound conjugate. The sirolimus bound anti-sirolimus antibody-β-galactosidase conjugate did not bind to the chrome particles but remained in the supernatant when a magnetic field was applied to the above reaction mixture to separate the solution from the chrome particles. The sirolimus-bound conjugate was detected by transferring the supernatant from the reaction vessel to a photometric cuvette and measuring the enzymatic rate of the conjugate in the presence of chlorophenol red-β-D-galactopyranoside (CPRG). The rate was measured bichromatically at 577 and 700 nm.

Comparison of Different Pretreatment Reagents

DMSO at 10 or 15% or MP at 10% with FKE were used to make separate pretreatment solutions (as discussed in detail above) for the ACMIA assay conducted on the DIMENSION® RxL analyzer for measuring sirolimus and its metabolites concentrations in whole blood samples. Another pretreatment solution was made without the above-mentioned organic solvents and FKE as control for the assay ("Control"). The pretreatment solutions spiked with and without the mentioned organic solvents were used to prepare the reagent cartridges for the sirolimus ACMIA assay on the DIMENSION® clinical chemistry analyzer. When the above-mentioned solvents and FKE were not used, all the metabolites showed high recoveries in the whole blood samples. In the following tables, the recoveries of sirolimus metabolites are reported as the percent of the recovery of the parent drug, sirolimus.

A substantial amount of sirolimus drug was released by FKE as witnessed by a large increase in the signal separation versus the no FKE control. The above experiment was performed with no organic solvent added and the reaction mixture was basically an aqueous solution. Addition of water miscible organic solvent such as alcohol or DMSO in the pretreatment reagent significantly reduced the metabolite cross-reactivity as indicated in the table. When no organic solvent was added, the metabolite cross-reactivity was the highest (the control in the Table 2 below). The results are summarized in Table 2.

TABLE 2

Metabolite* cross-reactivity using reagent containing varying organic solvent

| Treatment | % Solvent in Pretreatment Rgt** | % Solvent in Reaction Mixture | % Cross-Reactivity |
|---|---|---|---|
| Control | — | — | 180 |
| DMSO | 10 | 2.3 | 100 |
| DMSO | 15 | 3.4 | 88 |
| Methoxypropanol | 10 | 2.3 | 92 |

*27,39 Didesmethyl Sirolimus is used in this study
**The pretreatment reagent contains 15 μg/mL FK506 ester In the study referred to in Table 2 above, 27, 39 didesmethyl sirolimus was used for the organic solvent screening due to its relatively high hydrophilicity.

Table 3 illustrates the effect of FKE and organic solvent exemplified by DMSO on the percent cross-reactivity of sirolimus metabolites.

TABLE 3

Effect of FKE and DMSO on sirolimus metabolite cross-reactivity

| Metabolite | PT* with Neither FKE Nor DMSO | PT with 15 μg/mL/mL FKE | PT with 15 μg/mL FKE & 15% DMSO |
|---|---|---|---|
| 41-O-demethyl-(south) hydroxy sirolimus | 62 | 7 | −1 |
| 7-O-demethyl sirolimus | 6 | 7 | −3 |
| 11-hydroxy sirolimus | 315 | 78 | 35 |
| 11-hydroxy sirolimus (isomer of the above) | 114 | 34 | 9 |
| (south) hydroxy siro-2H | 17 | 11 | 0 |
| (N-oxide)-hydroxy sirolimus | 152 | 49 | 13 |
| (south) hydroxy siro-2H (isomer) | 32 | 7 | 0 |
| 41-O-demethyl-(south) dihydroxy siro-2H | | | |

TABLE 3-continued

Effect of FKE and DMSO on sirolimus metabolite cross-reactivity

| Metabolite | PT* with Neither FKE Nor DMSO | PT with 15 μg/mL/mL FKE | PT with 15 μg/mL FKE & 15% DMSO |
|---|---|---|---|
| 41-O-demethyl sirolimus | 48 | 39 | 40 |
| 32-O-desmethyl sirolimus | 34 | 8 | −3 |
| 27,39 Didesmethyl sirolimus | 569 | 165 | 88 |

*PT = Pretreatment Reagent

In the regular aqueous immunoassay reagents containing neither FKE nor DMSO, 315% cross-reactivity for 11-hydroxy sirolimus was detected due to its hydrophilic nature. In the presence of FKE but without DMSO, its cross-reactivity was 78%, significantly lower than that in the absence of FKE but higher than that when both FKE and DMSO were present. The cross-reactivity of 11-hydroxy sirolimus was the lowest (35%) when both FKE and DMSO are formulated in the pretreatment reagent. The cross-reactivity of other sirolimus metabolites followed the same pattern: cross-reactivity is the highest when the pretreatment reagent contains neither FKE nor DMSO, and the lowest when both are present.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for determining the presence or amount of an immunosuppressant drug in a medium suspected of containing an immunosuppressant drug, the method comprising:
   (a) providing in combination in a medium:
      (i) a sample suspected of containing a hydrophobic drug,
      (ii) a releasing agent for releasing the immunosuppressant drug and metabolites of the immunosuppressant drug from endogenous binding moieties that bind the immunosuppressant drug and the metabolites, and
      (iii) a selective solubility agent for the immunosuppressant drug and the metabolites wherein the selective solubility agent comprises a water miscible, non-volatile organic solvent and wherein the concentration of the selective solubility agent in the medium is sufficient to enhance the bioavailability of the immunosuppressant drug over that of the metabolites in the medium,
   (b) incubating the medium under conditions for enhancing the bioavailability of the hydrophobic drug over that of the metabolites in the medium,
   (c) adding to the medium (i) a photosensitizer incorporated in or attached to a first particle and being capable of generating singlet oxygen, and (ii) a chemiluminescent composition activatable by singlet oxygen and incorporated in or attached to a second particle, wherein an antibody that is specific for the immunosuppressant drug is attached to one of the first particle or the second particle and wherein an analog of the immunosuppressant drug is attached to the other of the first particle or the second particle,
   (d) subjecting the combination to conditions for binding of the antibody to the immunosuppressant drug, if present, or to the analog of the immunosuppressant drug wherein the binding brings the first particle and the second particle into close proximity and
   (e) irradiating the photosensitizer with light and detecting the amount of luminescence generated by the chemiluminescent composition, the amount of luminescence being inversely related to the amount of the immunosuppressant drug in the sample.

2. The method according to claim 1 wherein the immunosuppressant drug is selected from the group consisting of tacrolimus, cyclosporin, rapamycin and everolimus.

3. The method according to claim 1 wherein the selective solubility agent is a $C_2$ to $C_6$ polyol comprising 2 to 3 hydroxy groups, a $C_2$ to $C_6$ sulfoxide, a $C_2$ to $C_6$ sulfone or a $C_2$ to $C_6$ amide, a $C_2$ to $C_6$ mono-, di- and tri-ether of a polyol or a $C_2$ to $C_6$ mono-, di- and tri-esters of a polyol.

4. The method according to claim 1 wherein the selective solubility agent is ethylene glycol, glycerol, 1-methoxy-2-propanol, dimethyl sulfoxide, dimethyl sulfone or dimethylformamide.

5. The method according to claim 1 wherein the releasing agent is an analog of the immunosuppressant drug.

6. The method according to claim 1 wherein the antibody is associated with the first particle and wherein the second particle comprises an analog of the immunosuppressant drug attached thereto.

* * * * *